United States Patent [19]

Hutchinson et al.

[11] 4,231,849

[45] Nov. 4, 1980

[54] PROCESS FOR THE PREPARATION OF A PERFLUORINATED CYCLIC ETHER

[75] Inventors: John Hutchinson; Graham Whittaker, both of Runcorn, England

[73] Assignee: Imperial Chemical Industries Limited, London, England

[21] Appl. No.: 49,787

[22] Filed: Jun. 18, 1979

Related U.S. Application Data

[63] Continuation of Ser. No. 909,180, May 24, 1978, abandoned.

[30] Foreign Application Priority Data

Jun. 9, 1977 [GB] United Kingdom ............... 24084/77

[51] Int. Cl.³ .......................................... C07D 307/38
[52] U.S. Cl. ............................... 204/59 F; 260/347.91
[58] Field of Search ................... 260/347.91; 204/59 F

[56] References Cited

U.S. PATENT DOCUMENTS

| | | | |
|---|---|---|---|
| 2,594,272 | 4/1952 | Kauck et al. | 260/347.91 X |
| 2,644,823 | 7/1953 | Kauck et al. | 260/347.91 X |
| 2,678,319 | 5/1954 | Hause | 260/347.91 |
| 3,641,167 | 2/1972 | Moore et al. | 260/648 F |
| 3,679,709 | 7/1972 | Frick et al. | 260/347.91 |

FOREIGN PATENT DOCUMENTS

| | | |
|---|---|---|
| 1420428 | 1/1976 | United Kingdom . |
| 1450467 | 9/1976 | United Kingdom . |
| 1452212 | 10/1976 | United Kingdom . |

OTHER PUBLICATIONS

Houben-Weyl, Methoden der Organischen Chemie, vol. VI/3 (1965) George Thieme Verlag, Stuttgart, pp. 564–567.
Minnesota M&M, Chemical Abstracts, vol. 50 (1956) 26869.
Rzjabinin et al., Chemical Abstracts, vol. 72 (1970) 132,413h.
Kolenko et al., Chemical Abstracts, vol. 70 (1969) 87,422f.

*Primary Examiner*—Richard Raymond
*Attorney, Agent, or Firm*—Cushman, Darby & Cushman

[57] ABSTRACT

An inert fluid of high chemical stability which comprises a perfluorinated cyclic ether having the formula $C_{10}F_{20}O$, and its preparation by perfluorination of the corresponding ethylenically-unsaturated cyclic ether $C_{10}F_{18}O$ with cobalt trifluoride, electrochemically or with fluorine gas.

6 Claims, No Drawings

PROCESS FOR THE PREPARATION OF A PERFLUORINATED CYCLIC ETHER

This is a continuation, of application Ser. No. 909,180 filed May 24, 1978, now abandoned.

This invention relates to an inert fluid and to a process for the preparation of an inert fluid. The invention relates in particular to a perfluorinated cyclic ether of high boiling point having high chemical stability which is useful, for example, as a heat-transfer medium, lubricant, coolant, mould-release agent, dielectric material and in the formulation of blood substitutues.

According to the present invention there is provided an inert fluid of high chemical stability which comprises a perfluorinated cyclic ether having the formula

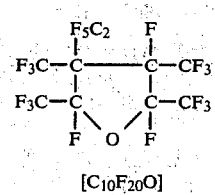

[$C_{10}F_{20}O$]

The inert fluid may be prepared by perfluorination of the corresponding ethylenically-unsaturated cyclic ether and such a process represents a further feature of the invention. The process comprises perfluorination of an ether of formula

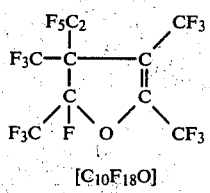

[$C_{10}F_{18}O$]

The inert ether starting material, $C_{10}F_{18}O$, can be prepared in good yield from the pentamer of tetrafluoroethylene by a process of hydrolysis and cyclisation.

Hydrolysis of tetrafluoroethylene pentamer with water in the presence of a tertiary nitrogen base and a polar organic solvent yields a fluorinated ketone of formula

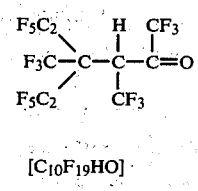

[$C_{10}F_{19}HO$]

i.e. nonadecafluoro-3,4-dimethyl-4-ethyl-3H-hexane-2-one. This process is described and claimed in United Kingdom Patent Specification No. 1 182 645, the disclosure of which is incorporated herein by reference. As described in Specification NO. 1.182,645, examples of suitable bases are triethylamine, diethylaniline and pyridine and suitable polar organic solvents include dimethylformamide, dimethylacetamide, diglyme (diethylene glycol dimethyl ether) and tetrahydrofuran. The molar ratio of pentamer to water is preferably less than 1.0 and of organic base to pentamer is preferably 1.0 or greater than 1.0. Temperatures in the range of 20° C. to 30° C. are preferred, though temperatures in the range 0° C. to 50° C. or even outside this range may be used.

The fluorinated ketone [$C_{10}F_{19}HO$] cyclises in the presence of a tertiary nitrogen base, for example triethylamine, at a temperature in the range of from 60° C. to 150° C. via the corresponding enolate anion.

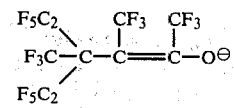

to yield the desired ethylenically-unsaturated cyclic ether [$C_{10}F_{18}O$] in high yield which may be up to 100% based on the fluorinated ketone starting material.

The conversion of the pentamer of tetrafluoroethylene to the fluorinated ketone may be carried out in two steps as described above, or it may be carried out in a single step. In the single step reaction, a dispersing agent will normally be included in the reaction mixture to aid dispersion of pentamer in the water. Any dispersion agent maybe employed which is chemically inert to the reactants and products, though we prefer to employ a surfactant derived from an oligomer of tetrafluoroethylene, for example a surfactant of formula $R_fOC_6H_4SO_3^-Na^{30}$ where $R_f$ is the residue $C_{10}F_{19}$—of tetrafluoroethylene pentamer since these have affinity for pentamer. A convenient technique comprises adding a tertiary nitrogen base, for example triethylamine, dropwise with cooling to a stirred dispersion of pentamer and polar aprotic organic solvent in water at a temperature of from 0° C. to 50° C., preferably 20° C. to 30° C. and stirring the resulting dispersion for a period of from 2 to 20 hours after the final addition of the tertiary nitrogen base. Distillation of the resulting mixture yields an azeotropic mixture of the tertiary nitrogen base and the cyclic ether. The single-step conversion of tetrafluoroethylene pentamer to the unsaturated cyclic ether $C_{10}F_{18}O$ followed by perfluorination of the cyclic ether to yield the inert fluid $C_{10}F_{20}O$ represents a preferred feature of the invention.

The unsaturated cyclic ether $C_{10}F_{18}O$ is converted into the inert fluid of the invention by fluorination to add fluorine ($F_2$) across the C=C double bond. The fluorination may be effected in a variety of ways, for example by heating the cyclic ether in the vapour phase with cobalt trifluoride, electrochemically or by direct reaction in an inert solvent with fluorine gas.

The process of fluorination using cobalt trifluoride comprises passing the cyclic ether $C_{10}F_{18}O$ in the vapour phase at a temperature of from 120° C. to 250° C. over heated cobalt trifluoride in a reactor tube, for example a metal tube, e.g. a nickel tube. Temperatures below 200° C. are preferred in order to obviate the risk of thermal degradation of the starting ether or the product ether, and the preferred temperature range is from 150° C. to 180° C. The optimum temperature within the above range can be determined by simple trial and error. The cyclic ether may be passed over the cobalt trifluoride with or without an inert diluent or carrier gas such as an inert gas, for example nitrogen. Typical dilution ratios are 1:1 of ether to diluent gas, and the rate of throughput of diluted ether is typically 0.25 to 1 ml per minute in a reactor tube containing about 2 kg of cobalt trifluoride. If desired, the gas stream may be recycled over the cobalt trifluoride.

Reaction of the unsaturated cyclic ether with the cobalt trifluoride is exothermic

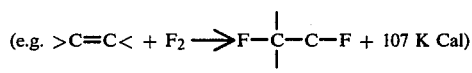

and the rate of throughput of the ether is controlled so that the temperature remains in the range stated hereinbefore. In steady-state operation it may be unnecessary to provide external heating or cooling. Yields of the perfluorinated cyclic ether in excess of 80% of theory can be achieved.

Electrochemical fluorination of organic compounds is a well known technique which involves dissolving the compound to be fluorinated in anhydrous hydrofluoric acid and electrolysing the resulting solution. The temperature of the electrolysis will usually be below 25° C., for example from −20° C. to 25° C., preferably from 0° C. to 20° C. and especially preferred temperatures are from about 2° C. to about 15° C.

The applied voltage for the electrolysis will usually be low, for example from 4 to 7 volts and electrolysis may be effected in a cell having means, for example a pump, for circulation and agitation of the electrolyte. If desired, a conductive salt may be incorporated in the electrolyte, for instance in cases where the ether to be fluorinated does not provide sufficient conductivity. However incorporating a conductive salt generally results in a decrease in the yield of desired product. The electrolysis may be carried out as a batch or continuous operation.

Reaction of the ether with elementary fluorine may be carried out in the conventional ways for gas-liquid reactions, the fluorine gas being introduced as bubbles, usually fine bubbles, into the lower end of a column or vessel containing the cyclic ether to be fluorinated or a solution thereof. Typical temperatures for this fluorination reaction are from −40° C. to 150° C., preferably from 0° C. to 100° C., depending however upon the particular ether to be fluorinated. Agitation means for the liquid may be provided to ensure thorough mixing of the gas and liquid phases, though the ascending gas bubbles usually provide adequate mixing. The ether may be dissolved in an inert solvent if desired or necessary, and suitable solvents include perfluorinated liquids, for example the perfluorinated alkane $C_8F_{18}$ obtained by fluorination of the tetramer of tetrafluoroethylene.

The dimensions of the liquid column and the flowrate of fluorine gas can be selected such that little or no unreacted fluorine gas passes through the column to take part in gaseous-phase reactions in the space above the liquid column. If substantial quantities of fluorine do pass through the liquid column, then the space above the liquid may be made as small as possible and cooled to minimize gas-phase reactions therein. Any fluorine gas passing through the column may be recycled or it may be passed through one or more further columns until it is completely reacted.

The perfluorinated product of the fluorination reaction, $C_{10}F_{20}O$, may be separated from residual unsaturated compounds and purified by reaction with an alcohol solution of a base, for example a solution of triethylamine in methanol, followed by distillation; however, distillation alone is normally adequate.

The perfluorinated cyclic ether product, $C_{10}F_{20}O$, is an inert, high-boiling liquid exhibiting high thermal and chemical stability. It shows no signs of decomposition when boiled in air for several weeks and is stable to strong alkalis, concentrated acids, solutions of potassium permanganate and solutions of amines.

The perfluorinated ether is readily emulsified in water using hydrocarbon emulsifying agents to yield stable emulsions having oxygen- and drug-carrying properties and suitable for use as blood substitutes. It exhibits high electrical breakdown strength and is a useful dielectric material; the electrical breakdown strength as measured according to BS.148/1972 is in excess of 50 kV.

The invention is illustrated but in no way limited by the following Examples.

EXAMPLE 1

Pentafluoroethylene pentamer ($C_{10}F_{10}$) (3.5 kg-7 moles), water (144 g-8 moles), diglyme (500 g) and surfactant (1 ml) were placed in a 5 l flanged flask fitted with stirrer and thermometer and immersed in a large bath of water at room temperature as a heat sink. The surfactant was the sodium salt of the sulphonic acid derivative of tetrafluoroethylene pentamer, $C_{10}F_{19}OC_6H_4SO_3^-Na^+$. The mixture was stirred vigorously to form an emulsion and triethylamine (1.414 kg-14 moles) was added dropwise over a period of about 4 hours such that the temperature of the reaction mixture was maintained between 28° C. and 30° C. The mixture was stirred overnight (about 16 hours) at room temperature after which the stirrer was removed and a still head fitted to the flask. The mixture in the flask was distilled using an isomantle heater, and the fraction collected which distilled over at 80° C. to 120° C. This was an azeotropic mixture of triethylamine and a cyclic enol ether.

The lower layer in the distillate was separated, washed with acetone (2×300 ml), then dilute hydrochloric acid to remove traces of triethylamine, then water, and then dried over sodium sulphate with a trace of decolourising charcoal. A water-clear product was obtained in 79% yield based on pentamer and gas-liquid chromatograph analysis of this product indicated a cyclic enol ether of greater than 95% purity.

Subsequent reaction of this cyclic enol ether with cobalt trifluoride (2 kg) at 160° to 170° C. in a nickel tube yielded a product containing 86% of a saturated cyclic ether (by g.l.c.) and distillation of this product yielded the ether $C_{10}F_{20}O$ of greater than 99% purity:

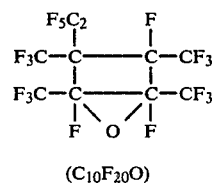

($C_{10}F_{20}O$)

The physical properties of the product were measured and are listed below, the results being shown in S I units:

| Property | |
|---|---|
| Molecular weight | 516 |
| Density (25° C.) | 1923 kg m$^{-3}$ |
| Boiling Point | 141.5° C. |

| Property | -continued |
| --- | --- |
| Dynamic Viscosity (25° C.) | 4.2 Ns m$^{-2}$ |
| Dynamic Viscosity (−40° C.) | 49.1 Ns m$^{-2}$ |
| Surface Tension (25° C.) | 0.02 Nm$^{-1}$ |
| Vapour pressure (25° C.)* | 1.694 kPa |
| Latent heat of Vaporisation at b p | 73245.0 J kg$^{-1}$ |
| Critical temperature | 279.0 ± 2.0° C. |
| Trouton's Constant | 21.8 |
| Dielectric Constant (1592 Hz, 23° C.) | 2.25 |
| Loss Tangent (1592 Hz, 23° C.) | <0.0006 |
| Specific conductivity | <1.3 × 10$^{-14}$ mho N$^{-1}$ |
| Volume resistivity (DC) (500 V for 1 min) | 1.3 × 10$^{-16}$ mho m$^{-1}$ |
| Electric Strength (IEC 156/1963) | 53 kV |
| Thermal Stability | <1% decomposition over 3 days at 250° C. in a glass tube. |

*Vapour pressure in Pascals (pa) at temp. T° C. calculated from the Antoine equation:

$\log_{10} Pa = \frac{A + B}{C + T}$ where

A = 10.3875
B = −2526.0971
C   327.8778

EXAMPLE 2

A 1 l capacity electrochemical fluorination cell, consisting of 9 anodes and 9 cathodes and with an effective anode area of 10 dm$^2$, was filled with a mixture of anhydrous HF (900 ml) and cyclic enol ether (45 g) prepared as described in Example 1. Electrolysis was carried out at 20° C. and applied voltage of 6v, the maximum current being 2 amps. An external cold trap at −78° C. was provided but no light residues were collected throughout the electrolysis.

After 18 hours, the current was switched off and the fluorochemical layer in the cell was run off and washed with water. The fluorochemical was analysed by infrared, N M R and gas chromatograph analysis each of which indicated that the major product was the saturated perfluorocyclic ether $C_{10}F_{20}O$ with residual starting material and some fragmentation products.

What we claim is:

1. A process for the preparation of a perfluorinated cyclic ether which comprises:
   (a) subjecting the pentamer of tetrafluoroethylene to a single step process of hydrolysis and cyclisation by adding a tertiary nitrogen base to a dispersion of the pentamer and a polar aprotic organic solvent in water at a temperature of from 0° C. to 50° C. to obtain the $C_{10}F_{18}O$ ether of formula

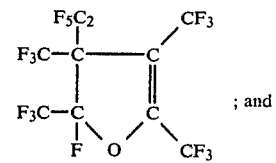
; and (b) perfluorinating the ether obtained in step (a) to obtain a perfluorinated cyclic $C_{10}F_{20}O$ ether having the formula:

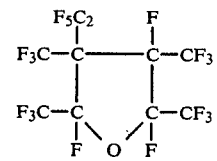

2. A process as claimed in claim 1 which comprises passing the ether $C_{10}F_{18}O$ in vapour phase at a temperature of from 120° C. to 250° C. over cobalt trifluoride.

3. A process as claimed in claim 2 wherein the ether is passed over cobalt trifluoride with an inert diluent or carrier gas.

4. A process as claimed in claim 1 wherein the ether $C_{10}F_{18}O$ is fluorinated electrochemically by electrolysing a solution of the ether in anhydrous hydrofluoric acid.

5. A process as claimed in claim 4 wherein the solution is electrolysed at a temperature of below 25° C. and at 4 to 7 volts.

6. A process as claimed in claim 1 wherein the fluorination is carried out with elementary fluorine at a temperature of from −40° C. to 150° C.

* * * * *